United States Patent [19]
Day

[11] Patent Number: 6,102,703
[45] Date of Patent: Aug. 15, 2000

[54] SELF-TAPPING DENTAL IMPLANT HAVING A BIO-REACTIVE COATING

[75] Inventor: Thomas H. Day, San Diego, Calif.

[73] Assignee: Sulzer Calcitek Inc., Carlsbad, Calif.

[21] Appl. No.: 09/250,378

[22] Filed: Feb. 15, 1999

[51] Int. Cl.[7] .................................................. A61C 8/00
[52] U.S. Cl. ............................................ 433/174; 433/173
[58] Field of Search ...................................... 433/172, 173, 433/174, 175, 176, 201.1, 199.1; 623/16, 11; 606/65, 66, 230, 231

[56] References Cited

U.S. PATENT DOCUMENTS

| | | | |
|---|---|---|---|
| 4,932,868 | 6/1990 | Linkow et al. | 433/174 |
| 5,571,017 | 11/1996 | Niznick | 433/174 |
| 5,727,943 | 3/1998 | Beaty et al. | 433/174 |
| 5,730,598 | 3/1998 | Story et al. | 433/201.1 |
| 5,863,201 | 1/1999 | Lazzara et al. | 433/201.1 |
| 5,879,161 | 3/1999 | Lazzara | 433/173 |
| 5,885,079 | 3/1999 | Niznick | 433/174 |
| 5,897,319 | 4/1999 | Wagner et al. | 433/174 |
| 5,947,735 | 9/1999 | Day | 433/173 |

*Primary Examiner*—Gene Mancene
*Assistant Examiner*—Pedro Philogene
*Attorney, Agent, or Firm*—Philip S. Lyren; Kenneth S. Barrow

[57] ABSTRACT

A self-tapping dental implant that is fully coated by hydroxylapatite. The dental implant includes a proximal end having a tool engaging region, a self-tapping distal end, and a generally cylindrical middle region that connects the two ends. The distal end, the middle region, and the self-tapping features are fully covered by a hydroxylapatite coating.

14 Claims, 2 Drawing Sheets

SELF-TAPPING DENTAL IMPLANT HAVING A BIO-REACTIVE COATING

FIELD OF THE INVENTION

The present invention relates generally to prosthetic implants, and particularly to self-tapping dental implants that are designed to facilitate osseointegration.

BACKGROUND OF THE INVENTION

A variety of dental implants currently are known and available. The implants are designed for insertion into the mandible or jawbone of a patient to support the mounting of a prosthesis. Generally, a cylindrical hole is formed in the mandible or jawbone of the patient, and the implant is disposed in the hole and allowed to undergo osseointegration.

A typical threaded dental implant has a generally cylindrical body with an unthreaded, annular portion at its proximal end. The remaining external surface of the generally cylindrical body is substantially threaded. The threads allow the dental implant to be turned into the cylindrical hole formed in the jawbone of the patient. The threads also secure the dental implant and promote osseointegration.

Insertion of the dental implant into the patient's jawbone may be simplified by the use of self-tapping implants. Such implants include self-tapping features often located at the distal end of the implant. Such features include, for example, recesses, such as flutes, that extend generally axially along the side wall of the distal end. The recesses interrupt the threads at the distal end and create cutting edges able to cut into the bone tissue along the periphery of the cylindrical hole formed in the jawbone. The recesses also provide spaces for holding any bone fragments or other tissue displaced during insertion of the implant.

Self-tapping implants are desirable because they immediately form a secure mechanical attachment to the bone tissue. They also promote direct integration of the bone tissue with the implant, i.e. osseointegration, through the more intimate contact formed as the self-tapping implant is threaded into the bone tissue.

Another aid to osseointegration is the use of a bio-reactive material as a coating on the implant. The implant may be made from a metallic material, such as titanium or a titanium alloy, to provide strength. This metallic material then may be coated with a material that promotes integration of the implant and surrounding bone tissue.

One bio-reactive agent that has been very successful in promoting osseointegration is hydroxylapatite (HA). HA is a synthetic form of biological apatite that is one of the major compounds occurring in human bones and teeth. Thus, it would be desirable to coat the outer surface of the implant with HA at least to the extent the implant is inserted into the bone tissue.

The use of bio-reactive materials, however, has been particularly problematic with self-tapping implants. As discussed by the inventor in U.S. Pat. No. 5,571,017, the cutting edges of the self-tapping implant must be sharp enough to shave bone chips. However, coating the self-tapping distal end with a bio-reactive material, such as HA, requires that the surface be substantially roughened by, for instance, blasting it with an aluminum oxide blast media. Blasting with aluminum oxide, however, rounds the cutting edges of the self-tapping features. This reduces the cutting efficiency of the self-tapping cutting edges. When this efficiency is reduced, greater torques are required to insert the implant, particularly when inserted into dense bone. The added torque can cause damage, including damage to the implant itself.

Additionally, the ceramic particles of the aluminum oxide blast media cannot readily be dissolved in solutions, such as acid solutions, or otherwise removed. This leaves particles between the metallic core material and the bio-reactive coating. The particles substantially reduce the bond or tensile strength between the metallic core and the bio-reactive coating, which can lead to fractured coatings, especially when subjected to the increased torques.

As disclosed in U.S. Pat. No. 5,571,017, an attempt has been made to overcome this problem by providing a relatively smooth, metallic distal end having self-tapping features that are free from any bio-reactive material. Only the middle portion of the dental implant, disposed between the proximal end and the self-tapping distal end, is provided with a relatively rough surface, such as by HA coating. This solution, however, does not permit coating of the dental implant with a bio-reactive material throughout the entire area of desired integration between bone tissue and implant.

It would be advantageous to be able to promote osseointegration along the entire surface area of the implant, when inserted into bone tissue, without creating the potential for damage by increased torques placed on the implant or fragile coatings.

SUMMARY OF THE INVENTION

The present invention features a dental implant that promotes osseointegration. The dental implant includes an implant body having a proximal end with a tool engaging region. The implant body also includes a distal end and a generally cylindrical middle region that extends between the proximal end and the distal end. Both the generally cylindrical middle region and the distal end have a roughened surface that is free of interfering particulates. A bio-reactive coating is disposed over the roughened surface to promote integration between bone tissue and the dental implant. Preferably, the dental implant includes self-tapping features.

According to another aspect of the present invention, a method is provided for making a dental implant that facilitates integration between the implant and surrounding bone tissue. The method includes providing an implant body having a proximal end, a middle region and a distal end. The method further includes forming a self-tapping region on the implant body. A blast media is used to blast the middle region and the distal end to create a roughened surface. The particulate matter from the blast media is then fully removed from this roughened surface. The method further includes coating both the middle region and the distal end with a bio-reactive material to aid in osseointegration.

According to a further aspect of the present invention, a method is provided for making a dental implant. The method includes providing an implant body having a proximal end, a middle region and a distal end. The method further includes creating a roughened surface on the implant body, and fully removing any bond-degrading matter from the roughened surface. The method also includes coating the roughened surface with a bio-reactive material, such as HA.

BRIEF DESCRIPTION OF THE DRAWINGS

The invention will hereafter be described with reference to the accompanying drawings, wherein like reference numerals denote like elements, and.

DESCRIPTION OF SPECIFIC EMBODIMENTS

Figure 1:
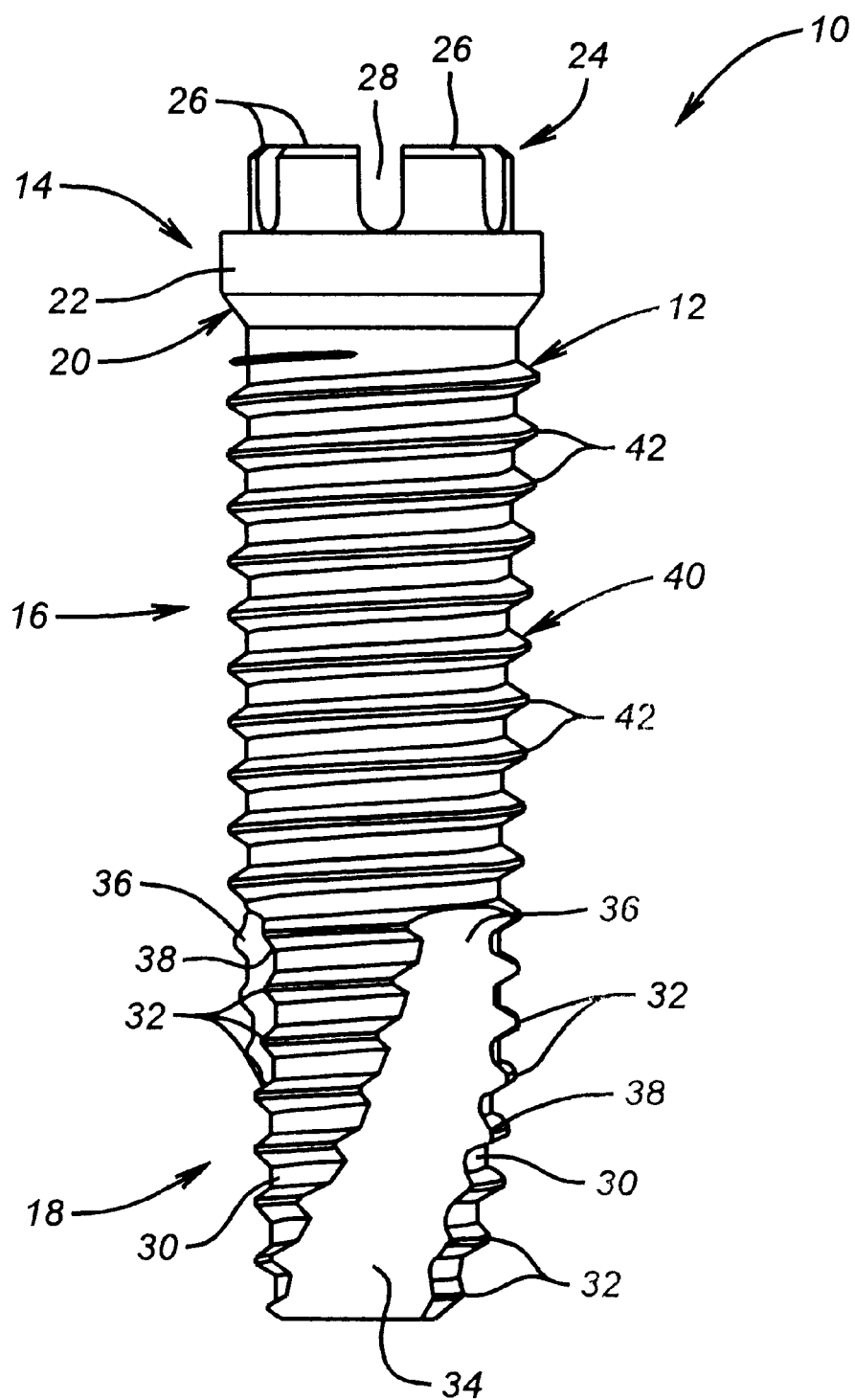
FIG. 1 is a front view of a self-tapping dental implant, according to a preferred embodiment of the present invention.

Referring generally to FIG. 1, a dental implant 10, according to a preferred embodiment of the present invention, is illustrated. The illustrated, exemplary dental implant 10 is a self-tapping implant having a generally cylindrical body 12 that includes a proximal end 14, a middle region 16 and a distal end 18.

Proximal end 14 includes a neck portion 20 that may have a relatively smooth annular segment 22. Extending upwardly from annular segment 22 is a tool engaging region 24.

Tool engaging region 24 is designed for engagement with a corresponding wrench or other dental tool. Tool engaging region 24 is configured to permit the dental tool to apply a torque to cylindrical body 12 as dental implant 10 is inserted into a corresponding, generally cylindrical opening formed in the jawbone of the patient. In the illustrated embodiment, tool engaging region 24 includes a plurality of splines 26 having gaps 28 therebetween. The splines 26 are engaged by an appropriate dental tool (not shown) so that dental implant 10 may be rotated to the desired position in surrounding bone tissue.

It should be noted that a variety of other tool engaging configurations may be used at tool engaging region 24. For example, a multisided extension, such as a hexagonal extension can be provided. Additionally, a multifaceted recess in proximal end 14 can be utilized. With any of these configurations, the dental tool is designed with appropriate corresponding features to impart the necessary torque to cylindrical body 12.

Distal end 18 preferably includes a threaded region 30 having a plurality of threads 32. Threaded region 30 is interrupted by at least one relief area 34, and preferably a plurality of relief areas 34. In the illustrated embodiment, relief areas 34 are in the form of flutes, such as helical flutes 36 that extend in a generally longitudinal or axial direction along the outer surface of distal end 18.

Relief areas 34, e.g. flutes 36, provide space or volume between the cylindrical body 12 and the bone tissue into which dental implant 10 is being inserted. This space permits the collection of bone chips and other tissue that are dislodged by at least one self-tapping cutting edge 38. In the illustrated embodiment, distal end 18 includes a plurality of cutting edges 38 formed along the interface between the trailing edge of each helical flute 36 and the adjacent threads 32.

The combination of cutting edges 38, relief areas 34 and threads 32 provide the exemplary dental implant 10 with a self-tapping ability. Specifically, in the illustrated embodiment, there are three helical flutes 36 separated by three portions of threaded region 30 and three cutting edges 38 to further facilitate the cutting and displacement of bone tissue as dental implant 10 is rotated to its desired position within the jaw of a patient.

Figure 2:
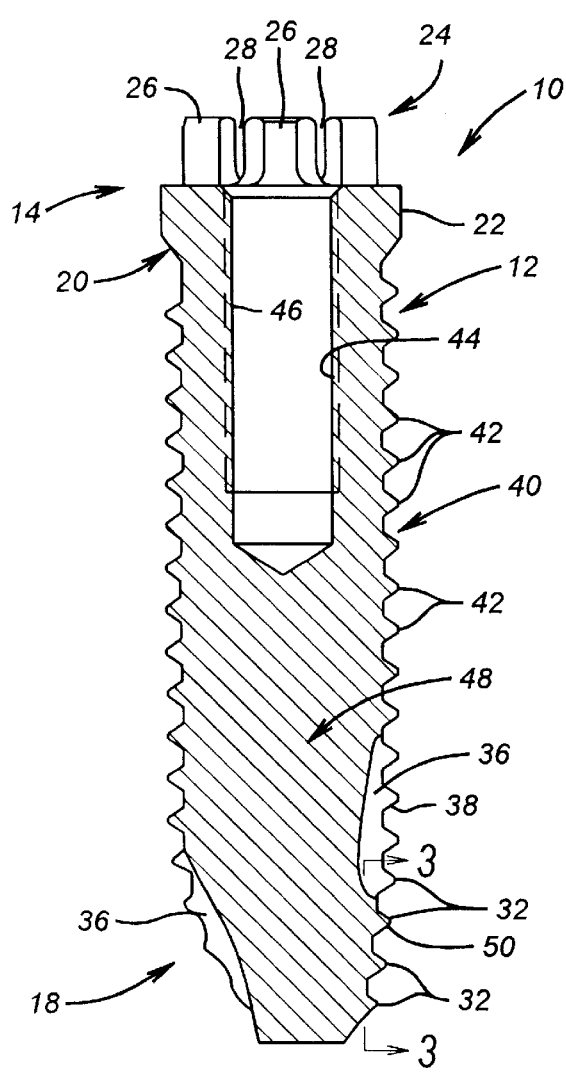
FIG. 2 is a cross-sectional view of the dental implant of FIG. 1, taken generally along its axis.

Proximal end 14 is connected to distal end 18 by middle region 16. Preferably, middle region 16 includes a threaded area 40 having a plurality of threads 42 that extend to and join threads 32 of distal end 18. Also, an internal passage 44 extends axially through proximal end 14 into middle region 16, as best illustrated in FIG. 2. Internal passage 44 preferably includes an internal threaded region 46 to which a healing screw and/or prosthetic may be secured.

Preferably, dental implant 10 includes a metallic core 48 made from an implant material such as titanium or a titanium alloy. Metallic core 48 is coated with a bio-reactive coating 50 along distal end 18 and preferably along the exterior surface of metallic core 48 throughout distal end 18 and middle region 16. The bio-reactive coating is designed to promote osseointegration, i.e. to promote integration between the implant and the surrounding bone tissue.

A preferred bio-reactive coating 50 is hydroxylapatite (HA). However, other coatings, such as titanium plasma spray, also can be applied. The coating is designed to optimize integration of bone and implant.

HA, for example, is very similar to naturally occurring biological apatite, which is one of the major compounds found in human bones and teeth. It has been found that the coating of HA over a metallic core 48 greatly facilitates integration of surrounding bone and tissue with dental implant 10. Bio-reactive coating 50 must be applied to metallic core 48, e.g. at distal end 18, without substantially interfering with the functionality of the self-tapping features. For example, the cutting edges 38 cannot be degraded such that detrimental torque is required when dental implant 10 is turned into a patient's jawbone. A preferred method for coating the metallic core 48 and cutting edges 38 can be described with reference to FIG. 4. It should be noted that the described method also can be used to coat implants or regions other than those having self-tapping features, such as middle region 16. Both middle region 16 and distal end 18 may be coated with bio-reactive coating 50 via the same process.

Figure 3:
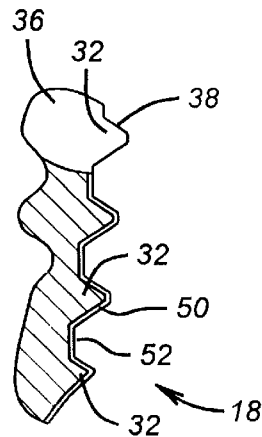
FIG. 3 is a partial cross-sectional view taken generally line 3—3 of FIG. 2.

Initially, an outer surface 52 (see FIG. 3) of metallic core 48 is roughened to a desired roughness, preferably substantially less than the roughness achieved during conventional blasting with aluminum oxide. Specifically, the preferred roughness of the roughened surface is approximately 40 to 50 microinches, as measured by the Ra (roughness average) method. In a preferred embodiment, outer surface 52 is blasted with HA powder as the blast media to create the desired roughened surface, as represented in block 54 of FIG. 4. The blasting is continued until a continuous portion of the implant, preferably including distal end 18 and middle region 16, is roughened to the desired degree of approximately 40 to 50 microinches, as measured by the Ra method.

Alternative blast media include calcium carbonate, sodium bicarbonate or other blast media that can be dissolved readily in a solution, typically an acidic solution. The solution should be able to substantially remove 100% of any particulate matter from the roughened surface, as described below. In another alternate embodiment, the roughened surface can be created by a chemical etch, such as acid etching.

Use of the preferred HA powder as the blast media substantially lessens the resultant roughness of outer surface 52 relative to the roughness obtained with conventional blast media, such as aluminum oxide. This approach permits cutting edges 38 to remain sharp, such that even after bio-reactive coating 50 is applied, there is no detrimental increase in the torque required to insert dental implant 10. Furthermore, the reduced roughness of outer surface 52 does not substantially reduce the tensile bond strength of the HA coating to the titanium substrate as one might expect. This phenomenon is believed to be due to the substantially complete removal of any bond-degrading impurities between the metallic core 48 and the bio-reactive coating 50.

Figure 4:
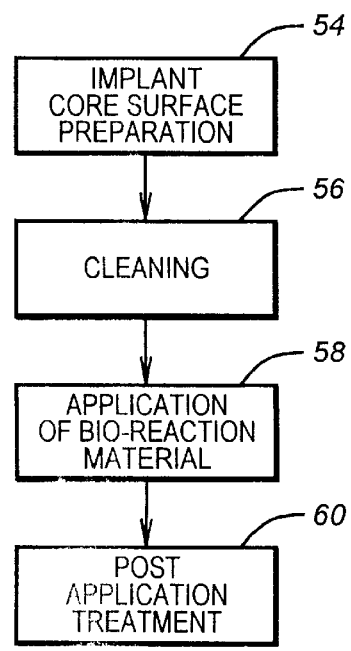
FIG. 4 is a block diagram illustrating a method of application, according to a preferred embodiment of the present invention.

Following roughening of the metallic core 48 by blasting, the residual HA powder is removed by rinsing the implant, as represented in block 56 of FIG. 4. Preferably, the implant is rinsed in a solution of 5% hydrochloric acid that dissolves the residual HA. Thoroughly rinsing dental implant 10 in the hydrochloric acid solution fully removes all particles of the blast media to permit application of the HA coating 50 without reducing the bond strength between the HA coating and the titanium substrate.

Once the implant is thoroughly rinsed, an HA coating, i.e. bio-reactive coating 50, is applied as represented in block 58 of FIG. 4. Preferably, the HA coating is applied by plasma spraying, as known to those of ordinary skill in the art. During the plasma spraying process, a stream of mixed gases pass through a high temperature electric arc. The electric arc ionizes the gases into a plasma flame, and crystalline HA feedstock powder is fed into the stream of mixed gases. The heat at least partially melts the HA feedstock powder which is propelled at a relatively high velocity against the outer surface 52 of dental implant 10. The molten particles of HA powder impinge against outer surface 52 and rigorously adhere to the particulate-free surface to form a relatively thin coating of HA.

After the HA coating is applied to distal end 18 and middle region 16, the dental implant 10 may be processed further to increase the crystalline HA content of coating 50, as represented in block 60 of FIG. 4. It is advantageous to increase the crystalline content of the HA coating, because it is known that highly crystalline HA has an in vitro stability that is much higher than non-crystalline HA. It is preferred that the crystalline content of the HA coating be increased to at least about 90% by weight of crystalline HA. Most preferably, the crystalline HA content is increased to at least about 97% by weight. A preferred method of increasing the crystalline HA content is described in U.S. Pat. No. 5,730,598, issued on Mar. 24, 1998, which is incorporated herein by reference.

It will be understood that the foregoing description is of a preferred exemplary embodiment of this invention, and that the invention is not limited to the specific form shown. For example, a variety of core materials may be used for the dental implant; other blast media may be used if they are generally able to achieve the same roughness of the metallic core and yet be fully removed during cleaning; other bio-reactive coatings may be used; and a variety of dental implant designs and self-tapping feature designs may be utilized. For example, the self-tapping features are not necessarily at the distal end of the implant. The self-tapping features may be disposed in the middle region, for example, as with a "stepped" implant. Additionally, this process can enhance the bond strength between the bio-reactive coating and the implant body in dental implants that have no self-tapping features. These and other modifications may be made in the design and arrangement of the elements without departing from the scope of the invention as expressed in the appended claims.

What is claimed is:

1. A dental implant, comprising:
   an implant body having a proximal end with a tool engaging region, a cylindrical middle region, and a distal end;
   a plurality of self-tapping features on the implant body, wherein the self-tapping features have a roughened surface free of particulates; and
   a bio-reactive coating applied directly to the self-tapping features.

2. The dental implant as recited in claim 1, wherein the middle region and the distal end are threaded and have a roughened surface and a bio-reactive coating.

3. The dental implant as recited in claim 2, wherein the self-tapping features extend from the distal end to the middle region.

4. The dental implant as recited in claim 3, wherein the bio-reactive coating comprises HA.

5. A method for coating a dental implant, comprising the steps of:
   providing a dental implant having an implant body with a proximal end, a middle region, a distal end, and a self-tapping region;
   roughening the self-tapping region;
   removing any particulates on the self-tapping region; and
   coating the self-tapping region a bio-reactive material to aid osseointegration.

6. The method as recited in claim 5, wherein:
   the roughening step includes blasting the implant body with an HA powder; and
   the coating step includes plasma spraying with an HA material.

7. The method as recited in claim 6, wherein coating includes spraying with an at least one of calcium carbonate, sodium bicarbonate, or partially crystalline HA material.

8. The method as recited in claim 5, wherein the removing step includes dissolving particles left on the self-tapping region from the roughening step.

9. The method as recited in claim 8, wherein the dissolving includes rinsing the implant with a hydrochloric acid solution.

10. The method as recited in claim 6, wherein blasting includes roughening the self-tapping region to a roughness in the range from approximately 40 to 50 microinches as measured using the Ra method.

11. A method for coating a dental implant, comprising the steps of:
    providing an implant body having a proximal end, a middle region, a distal end, and a self-tapping region located at the distal end;
    creating a roughened surface on the distal end of the implant body;
    removing any bond-degrading matter from the roughened surface; and
    coating the distal end with a bio-reactive material.

12. The method as recited in claim 11, wherein the step of creating a roughened surface includes plasma spraying the distal end with HA.

13. The method as recited in claim 12, wherein the roughened surface has a roughness in the range from approximately 40 to 50 microinches as measured using the Ra method.

14. The method as recited in claim 12, wherein the bio-reactive material is HA.

* * * * *